(12) United States Patent
Gilo et al.

(10) Patent No.: US 8,496,966 B2
(45) Date of Patent: *Jul. 30, 2013

(54) QUICK DISSOLVING CARRIER GRANULES

(75) Inventors: Yechiel Gilo, Greensboro, NC (US); Steven G. Myers, Mocksville, NC (US)

(73) Assignee: Cycle Group, Inc., Mocksville, NC (US)

( * ) Notice: Subject to any disclaimer, the term of this patent is extended or adjusted under 35 U.S.C. 154(b) by 1348 days.

This patent is subject to a terminal disclaimer.

(21) Appl. No.: 11/256,099

(22) Filed: Oct. 24, 2005

(65) Prior Publication Data

US 2007/0098752 A1      May 3, 2007

(51) Int. Cl.
*A61K 9/14* (2006.01)
*A61K 9/50* (2006.01)

(52) U.S. Cl.
USPC .................. 424/489; 424/499; 424/450

(58) Field of Classification Search
None
See application file for complete search history.

(56) References Cited

U.S. PATENT DOCUMENTS

| | | | |
|---|---|---|---|
| 5,019,564 A | 5/1991 | Lowe et al. | |
| 5,078,779 A | 1/1992 | Van de Walle et al. | |
| 5,242,690 A | 9/1993 | Moechnig | |
| 5,970,916 A * | 10/1999 | Yoder et al. | 119/173 |
| 6,030,565 A | 2/2000 | Golan | |
| 6,194,065 B1 | 2/2001 | Golan | |
| 6,231,660 B1 | 5/2001 | Welshimer et al. | |
| 6,410,305 B1 * | 6/2002 | Miller et al. | 435/268 |
| 6,572,920 B1 | 6/2003 | Eitan et al. | |
| 6,583,099 B2 * | 6/2003 | Christensen, Jr. | 510/392 |
| 6,613,138 B2 | 9/2003 | Welshimer et al. | |
| 6,745,720 B2 | 6/2004 | Rasner et al. | |
| 2003/0170905 A1 | 9/2003 | Kamyshny et al. | |
| 2004/0112297 A1 | 6/2004 | Rasner et al. | |
| 2005/0132968 A1 * | 6/2005 | Swank | 119/171 |
| 2005/0220885 A1 | 10/2005 | Gilo et al. | |

OTHER PUBLICATIONS

Sweet, Palmer C. Mining and Processing By-product Resources in Virginia. Virginia Minerals. 1998: 44(2). pp. 9-16.*

* cited by examiner

*Primary Examiner* — Rachael E Bredefeld
(74) *Attorney, Agent, or Firm* — Birch, Stewart, Kolasch & Birch, LLP

(57) ABSTRACT

A quickly dissolving carrier granule made up of wood fibers, mineral filler, and starch-based or dextrin-based adhesive binder. The wood fibers in these granules are preferably wood fibers ranging from about 10 microns to about 2 mm in length. Typically, at least about 35 weight-% of the fibers are retained on a 50-Mesh U.S. Sieve Series screen. The wood fibers in this invention are derived from sources that are substantially free of resins such as urea-formaldehyde resin and of diphenylmethane diisocyanate resin. Typical binders are soluble dextrin binders or a viscous corn starch, wheat starch, rice starch, tapioca starch, potato starch, or sago starch binders. The granules have a Resistance to Attrition of at least 90%. Also disclosed is a method of making such granules. The disclosure also describes carrier granule compositions which are made up of from 10 to 90 weight-% of carrier granules wherein the binder is a dextrin binder and from 90 to 10 weight-% of carrier granules wherein the binder is a food-based or industrial-based native starch.

9 Claims, No Drawings

QUICK DISSOLVING CARRIER GRANULES

This invention relates to the manufacture of carrier granules suitable for use as carriers for herbicides, insecticides, and fungicides, for plant growth regulators, and for other biologically active compounds. This invention is particularly concerned with applications in which quick release of chemicals, such as by dissolution of the granules that carry the chemicals, is required.

Various different types of granules are currently used for carrier and delivery applications. Patents disclosing granules include the following.

U.S. Pat. No. 5,019,564 discloses granules formed by the agitated agglomeration of slurries containing plant fibers and mineral fillers. These granules are utilized as carriers for biologically active chemical agents.

U.S. Pat. No. 5,242,690 discloses granular carrier compositions that include grain dust and a binder of calcium or sodium lignosulfonate, the compositions being useful as carriers for biologically active chemical agents.

U.S. Pat. No. 6,030,565 discloses wood fiber-based agglomerates intended for use, e.g., as animal litter substrates (30 weight-% wood waste as an organic fibrous material, 63 weight-% quarry dust as a mineral filler, and 8 weight-% paper pulp waste binder) and industrial liquid absorbents (30 weight-% wood waste as an organic fibrous material, 60 weight-% quarry dust as a mineral filler, 8 weight-% binder, and 2 weight-% fire retardant).

U.S. Pat. No. 6,231,660 B1 discloses granules that include one or more mineral components having a bulk density greater than about 70 pounds per cubic foot, one or more "light weight additives", and one or more water soluble binders. The patent teaches that the lightweight additives should be a non-fibrous material, because fibrous material can adversely impact the dispersibility and the flow characteristics of the finished granular substrate. The terminology "light weight additive" is vague. However, the patent provides some idea of what is meant by that terminology: "The light weight additives are preferably selected form the group consisting of expanded silica, fly ash, hydrated lime, wheat flour, wood flour, ground wheat straw, cellulose and soy flour." Column 4, lines 33-36. The patentee explains what."wood flour" involves in the following words: "A preferred embodiment includes the use of wood flour resulting from finely milled wood particle board. The wood particle board contains approximately 10 wt % of a urea-formaldehyde resin. Another preferred embodiment includes the use of wheat straw flour resulting from finely milled wheat straw particle board. The wheat straw particle board contains a diphenyl-methane diisocyanate resin." Column 4, lines 40-46. The Examples in the patent disclose as binders brewers condensed solubles, calcium lignosulfonate, cane molasses, beet syrup, beet molasses, hydrolyzed collagen, soy solubles, whey, sodium carbonate lignin, protein amino acids, hemi-cellulose extract, sodium carboxymethyl cellulose, corn starch mixed with sodium carboxymethyl cellulose, and Baka-Snak.

There is an unmet need for carrier granules that will better satisfy the needs of the agricultural industry. In particular, there is a need for carrier granules that are stable during storage and handling but that readily dissolve or disintegrate after they are applied to the soil or to the lawn.

SUMMARY OF THE INVENTION

This invention provides carrier granules that are suitable for use as carriers for the home lawn and garden market, the turf professional market, and the broader agricultural market. The trend in recent years has been for pesticidal applications to lawn, garden, and similar areas—both in private homes and in public areas—to employ carrier granules rather than liquid sprays. This is in response to environmental dangers associated with spray application of pesticides. However, as noted above, currently available carrier granules lack optimum flexibility with respect to the manner in which they perform in the field.

While some pesticidal application require the granules to remain intact for weeks or even months after they are applied (slow release applications), other applications require a very quick release of the chemicals from the granules. This quick release can be achieved by dissolution of the granules, which releases the pesticidal chemicals associated with the granules to the surrounding areas. Such "quick release" granules tend to lack the appropriate strength characteristics necessary to resist the attrition cause by handling of the granules during production, packaging, transportation, and storage.

The present invention provides a fast dissolving granule that retains excellent strength and attrition-resistance characteristics.

Specifically, the present invention provides a quickly dissolving carrier granule made up of 12-40 weight-% of wood fibers having a bulk density of less than 20 pounds per cubic foot, 50-85 weight-% of mineral filler having a bulk density of less than 75 pounds per cubic foot, and 3-12 weight-% of a starch-based or dextrin-based adhesive binder. The wood fibers used in the granules of this invention are preferably wood fibers ranging from about 10 microns to about 2 mm in length. Preferably also, at least about 35 weight-% of the fibers are retained on a 50-Mesh U.S. Sieve Series screen. The binder in this invention may be, for instance, a soluble dextrin binder or a viscous corn starch, wheat starch, rice starch, tapioca starch, potato starch, or sago starch binder. The granule of this invention passes through a 10-Mesh U.S. Sieve Series screen and is retained on a 40-Mesh U.S. Sieve Series screen. The granule has a moisture content of less than 5 weight-% and a Resistance to Attrition of at least 90%. The carrier granule of this invention is substantially completely dissolved or dispersed by immersion in water for 1 hour.

When the binder of this invention is a soluble dextrin binder, it may be selected from the group consisting of dextrin, polydextrin, and malto-dextrin. When the binder in the present quickly dissolving granules is a viscous binder of food-based starch, it may be selected from the group consisting of binders derived from corn starch, wheat starch, potato starch, tapioca starch, and rice starch (preferably from corn native starches or tapioca starch).

In this embodiment of the invention, the mineral filler used in the carrier granule is selected from the group consisting of kaolin, titanium dioxide, sodium bicarbonate, calcium carbonate, lime, fly ash, dolomite, gypsum, and mixtures thereof. Particularly preferred as mineral fillers are calcium carbonate or lime having a particle size in the range 10 to 100 microns.

In a particularly preferred subgenus of the quickly dissolving carrier granules of this embodiment of the invention, the ratio of wood fiber to mineral filler ranges from 18:82 through 25:75, and the granule comprises 3-12 weight-% binder. These granules are substantially completely dissolved or dispersed by immersion in water for less than 5 minutes.

The present invention also contemplates a method for making carrier granules by: (a) forming a mixture comprising 12-40 weight-% wood fibers having a bulk density of less than 20 pounds per cubic foot, said fibers having a moisture content of less than 15 weight-%, 55-85 weight-% of mineral filler having a moisture content of less than 12 weight-% and a bulk density of less than 75 pounds per cubic foot, and 3-12 weight-% of a binder selected from the group consisting of dextrin binders and food- and industrial-based native starch binders; (b) agglomerating said mixture by conditioning and agglomerating the mixture in a pin mixer to form small particles followed by agglomerating the mixture in a disc or pan pelletizer to form substantially spherical granules; (c) drying said granules to a moisture content of less than about 5 weight-%; and (d) screening said granules to select granules that pass through a 10-Mesh U.S. Sieve Series screen and are retained on a 40-Mesh U.S. Sieve Series screen.

Another embodiment of the present invention is a quickly dissolving carrier granule which employs granite fines as a filler. These granules contain 15-35 weight-% of wood fibers having a bulk density of less than 20 pounds per cubic foot, 50-85 weight-% of mineral filler comprising granite fines having a bulk density of less than 75 pounds per cubic foot, and 3-12 weight-% of a starch-based or dextrin-based adhesive binder. These granules pass through a 10-Mesh U.S. Sieve Series screen and are retained on a 40-Mesh U.S. Sieve Series screen, have a moisture content of less than 5 weight-%, have a Resistance to Attrition of at least 90%, and are substantially completely dissolved or dispersed by immersion in water for 1 hour.

The wood fibers and binders that are employed in this embodiment of the invention are the same as those described above. In a preferred subgenus of this invention, the ratio of wood fibers to mineral filler ranges from 18:82 through 25:75, the granules comprise 6-14 weight-% binder, and the granules are substantially completely dissolved or dispersed by immersion in water for less than 5 minutes.

The carrier granules of this invention are substantially free of resins such as urea-formaldehyde resin and of diphenylmethane diisocyanate resin. That is, in the present invention, resins such as those named are not employed to assist in producing a granular substrate that does not degrade during handling and that breaks down upon exposure to water. The granules of the present invention do not degrade during handling, and they break down readily upon exposure to water, but they depend for those properties upon their primary fiber and binder ingredients rather than upon any resin derived for instance from a source of their fiber component.

Yet another embodiment of the present invention is a carrier granule composition made up of from 10 to 90 weight-% of carrier granules as described above wherein the binder is a dextrin binder, and from 90 to 10 weight-% of a carrier granule as described above wherein the binder is a food-based or industrial-based native starch.

DESCRIPTION OF PREFERRED EMBODIMENTS

In order to enable the granules of the present invention to be fast-dissolving, the granules are provided with an open structure. This open structure in the granules of the present invention is achieved by means of the wood fibers which are an essential component of the granules. The wood fibers are combined with mineral filler to provide optimum bulk density to the granule. A key feature of the granules of the present invention is the type of binder employed to agglomerate the wood fibers and mineral filler together. The binders used in this invention provide the granules with strength and resistance to attrition while the granules are being handled, but lose their binding properties in the presence of water. The previously mentioned openness or porosity of the granules of this invention enables water to penetrate deeply inside the granules to break the binder ties quickly.

Binders suitable for use in the present invention include starch-based and dextrin-based adhesive binders. Starch and dextrin adhesive binder compositions are readily available, low in cost, and easy to apply from water dispersion. Formulated starch and dextrin adhesive binders can be applied hot or cold. These binders are generally supplied as powder and mixed with water prior to use. Starch and dextrin cure by the loss of moisture to a thermosetting structure. Accordingly, they have good heat resistance.

Dextrin is a starch that has been processed further. Both starch and dextrin are carbohydrate polymers. Starch is a natural polymer (a polysaccharide) derived from the seeds, roots, and leaves of plants. The plants that yield starch in sufficient quantities to be economical are corn, wheat, potato, rice, tapioca, and sago.

Starches are carbohydrate polymers, consisting of anhydroglucose units linked together by glucosidic bonds. Starch is made up of two major types of polymers, known as amylose and amylopectin. Amylose is primarily linear, containing from 200 to 2,000 anhydroglucose units. Amylopectin is a branched polymer, also connected by glucosidic linkages, but with periodic branch points. Amylopectin is typically much larger than amylose, with molecular weights in the millions. Amylose and amylopectin contain an abundance of hydroxyl groups, creating a highly hydrophilic (or water-loving) polymer that readily absorbs moisture and disperses well in water. Because amylose is linear, it has a tendency to align itself in a parallel nature with other amylose chains, leading to precipitation (in dilute solutions) or retrogradation (in high solids or gels). On the plus side, it also can lead to the formation of strong films, which are extremely useful in certain food applications. The negative side is that amylose can detract from clearer food products by contributing opacity, and also tends to mask delicate flavors. Because of its branching, amylopectin forms clearer gels—often favored in the food industry—that do not form strong films or gels. Retrogradation occurs less readily.

In the native form, most starches contain 18% to 28% amylose, with the remainder as amylopectin. Corn and wheat starches contain approximately 28% amylose, while potato, tapioca, and rice varieties are closer to 20%.

Heating in water is the simplest method of breaking up starch granules. On heating in water, starch granules first swell and then burst open with a resulting thickening of the suspension. The temperature at which this thickening of the suspension occurs is called the gelation temperature. In this form, the starch is not a true solution but a colloidal suspension. The starches of the native starch type usable herein are natural polymers having long molecular chains. The molecules in the native starch polymers are clustered together to form strong chains, thus providing binders having strength, elasticity, and slower aqueous break down properties.

The starches from the dextrin family are natural polymers having short molecular chains.

Dextrin adhesive binders are manufactured by dry-roasting starch in the presence of an acid catalyst. Through treatments with heat and acid, the starch molecules are hydrolyzed into small fragments and then re-polymerized into highly branched, readily soluble polymer molecules of moderate size. Cornstarch is commonly used to make dextrin adhesive binders, although other starches are also sometimes used. Dextrin binders have strength, rapid absorption, and the desired quick aqueous breakdown properties.

In general, starch granules differ in size and shape, depending on the plant source. Granules of rice starch are small (3 to 8 μm), polygonal in shape, and tend to aggregate, thereby forming clusters. Corn starch granules are slightly larger (approximately 15 µm) and are round to polygonal. Tapioca granules are even larger (approximately 20 µm), with rounded shapes that are truncated at one end. Wheat starch tends to cluster in several size ranges: Normal granules are approximately 18 µm; larger granules average about 24 µm; and smaller granules average approximately 7 to 8 µm, with round to elliptical shapes. Potato starches are oval and very large, averaging 30 to 50 µm. These variations in granule size and shape provide distinct differences not only in appearance, but in viscosity development, stability, mouthfeel, and rate of gelatinization in products.

One embodiment of the present invention is a mixture of carrier granules, in which some granules are made with dextrin binders and are quick dissolving, while other granules are made with native starch granules, and dissolve more slowly. This provides users with the opportunity to tailor pesticidal release properties to fit desired time profiles.

In the present invention, the wood (cellulose) fibers serve as a structural skeleton for the granules. They also contribute to the formation of cavities (pores) within the granules, thus reducing product weight and improving the release of active chemicals (pesticides, fertilizers, etc.). The fiber size distribution of the wood fibers in the granules will preferably provide a combination of short and long fibers that will contribute to the development of a strong yet open structure in the granules. The dry wood fibers in the granule will generally have a length of up to 2 millimeters, with a minimum of 35% of the fibers being retained on a 50-Mesh U.S. Sieve Series screen. For a tabulation of U.S. Sieve Series screen nomenclature, see Perry's Chemical Engineering Handbook, 6th Ed., McGraw-Hill, Inc., New York, N.Y. (1984), p. 21-15 (Table 21-6). Inasmuch as the median granule size in this invention is approximately 20-Mesh, which=0.841 mm, such fibers are—in the context of this invention and compared to flour-like fibers—"long". The wood fibers preferably have a moisture content of less than 15 weight-%. Long "fluffy" wood fibers which weigh less than 20 pounds per cubic foot are preferred.

Wood fibers usable in accordance with this invention may be made from sawdust and similar waste or by-product of hardwood and softwood manufacturing facilities. Fibers in the wood waste as received vary in length, e.g. from 15 mm to 10 microns. The required size fibers for this invention (from about 10 microns to about 2 mm) are obtained by passing the wood through a hammer mill and employing screening to select out fibers of the desired sizes.

The mineral in the granule is a filler which gives the granule its desired specific weight. Fillers that may be used include kaolin, titanium dioxide, sodium bicarbonate, calcium carbonate, and mixtures thereof. In a preferred embodiment of the invention, this filler is a lime derivative, e.g., lime itself, fly ash, dolomite, calcium carbonate, gypsum, and mixtures thereof. However, any inert, preferably low pH mineral that has a high specific weight and is capable of supplying fine particles may be. Calcium carbonate or agricultural lime is currently preferred. Typically, the dry mineral filler has a particle size range within the range 10 to 100 microns, and has a moisture content of less than 12 weight-%. Generally, any mineral filler with particles smaller than 150-Mesh U.S. Sieve Series will be operative in the present invention. In accordance with the present invention, the mineral filler has a bulk density of less than about 75 pounds per cubic foot.

Another class of mineral filler that can be used in the present invention is granite fines. Granite fines are available as a by-product from granite quarries and from operations where granite is cut or engraved. Granite fines thus are economical, and their use in the present invention has environmental advantages. The liquid absorption of granite is lower than that of lime or dolomite or calcium carbonate. Accordingly, in agglomeration and palletizing and other such granulation processes that employ moisture, the total amount of water used will be significantly less when granite fines are used as the filler rather than one of the afore-mentioned conventional fillers. This has an impact also on energy costs, since less energy will be needed to dry the granules. Another advantage of granite fines is their low pH. Granules used in cat litter or as carriers for pesticides preferably have low pH, so that often—when using a mineral with a high pH, such as calcium carbonate or lime—a pH buffer or a low pH additive is necessary. Finally, granite fines are chemically stable. In some case, chemical ingredients applied on granules will react with fillers such as calcium carbonate. The use of granite fines as fillers avoids undesired chemical interactions.

MANUFACTURE. To manufacture the granules of this invention, a homogenous dry mixture is prepared and then is pelletized and the pellets are dried and screened. More specifically, this invention contemplates a method for making a granule, which method includes the steps of: forming a mixture comprising dry wood fibers, dry mineral filler, and binder; pelletizing the mixture in a pin mixer and disc or pan pelletizer to form substantially spherical granules; and screening the granules to select granules which, for instance, pass a 10-Mesh U.S. Sieve Series screen but are retained on a 40-Mesh U.S. Sieve Series screen.

Dry Blends Preparation. In this stage, a bulk mixture of components in the desired weight ratios is prepared. Each scheduled component is dosed in its turn from a weighing station into a hopper. Once all of the components are in the hopper, the unmixed batch is conveyed to a mixer. The components, which at this point differ in bulk density and texture, require intensive mixing to achieve a good mix. A typical mixing procedure mixes each batch for from 90 to 120 seconds in a plowshare high-speed mixer. Once well mixed, each batch is conveyed to a surge and combined with other batches having the same component weight ratios.

Agglomeration. This stage creates granules from a dry blend of granule components. Dry blend is dosed continuously into a pin mixer. At the same time, water is injected into the pin mixer at several different locations. High-speed rotation of the wetted blend within the pin mixer creates "seeds" or small particles of the blended materials. During this step, the wood fibers are "conditioned" or softened by the water. This conditioning step is important in the present invention due to our use of long fibers. The wetted blend is then transferred to an agglomeration pan, where agglomeration is completed. In the agglomeration pan, more material accumulates around each seed, and more waters is added, creating a more spherical granule. Parameters such as granule size and weight can be controlled in this stage by changing the blend/water ratio as well as by changing the speed and/or inclination of the pin mixer and/or the agglomeration pan.

Compacting. At this point, the wet granules are compacted in a rotating drum. This imparts their final strength and bulk density characteristics. Variations in strength and/or bulk density can be achieved by adjusting the length of time and/or speed of rotation, following empirical determination of relationships between rotation and those characteristics.

Drying. In this stage, wet granules are dried to reach their final moisture level. The open structure of the granules reduces significantly the drying time and the energy required for drying. Perforated belt dryers or fluidized bed dryers are employed to remove the necessary amount of moisture from each granule. The desired final moisture content, generally from about 2% to about 4%, is achieved by controlling the air temperature, air speed, and granule throughput rate in the dryer.

Dry Screening. Once dried, the batch of granules of this invention may be screened to remove both oversized granules and undersized granules, and to provide a product having a uniform granule size profile. Those skilled in the art are familiar with appropriate screening technology and the use of such devices as vibrating and rolling machines. The oversized and undersized granules are recycled to the Dry Blend Preparation stage.

PREFERRED FORMULATIONS. Currently preferred formulation comprises 18-25 weight-% wood fiber and 82-75 weight-% mineral. The amount of binder in these preferred formulations is 3-12 weight-%, based on the total amount of mineral and wood fiber.

The wood fiber is typically wood fiber generated as a by-product by the furniture industry. At least 80 weight-% of the wood fiber employed in the preferred formulations is from hardwood. Up to 20 weight-% of the wood fiber may be softwood-derived. Urea or formaldehyde are not acceptable, so that a wood component derived from such sources as particleboard (which may contains high percentage of such chemicals) is not employed here. In the preferred formulations of the present invention, the wood fiber as received from the furniture industry is ground in a hammermill and then screened with a #30 Mesh screen. The bulk density of the ground wood fiber is typically in the range 12-16 pounds per cubic foot.

In the preferred formulations, the mineral is typically a member of the lime family, such as dolomite or some other high calcium mineral. Granite fines can alternatively be used here. The role of the mineral in the quick-dissolving carrier granules of the present invention is as a filler, to give weight to the finished product. The mineral typically has a bulk density in the range 65-75 pounds per cubic foot. The moisture content of the mineral component in this invention is typically less than 12%. A minimum of 70% of the mineral filler used herein will pass through a #200 Mesh screen.

The binder component gives strength and elasticity to the granules. In the present invention, the binder is also selected to control the rate of dissolvability of the carrier granules. The currently preferred binder herein is dextrin. The dextrin is processed through slow roasting and/or by the use of chemical additives, to chop the starch molecules in order to provide a more soluble binder. The dextrin is typically used herein in the form of a dry powder.

Typically, these preferred formulations have a finished product bulk density in the range 38-42 pounds per cubic foot; a finished product ASTM attrition rating of 97% or above, a finished product internal visual dust test result of 3 seconds, and a finished product angle of repose of 30-39°.

SPECIFIC FORMULATIONS. Typical specific formulations are set forth below. Those skilled in the art will recognize that the specific ingredients recited and their relative amounts can be varied widely while still making available the benefits provided by the present invention.

EXAMPLE #1

| Components | Weight-% |
| --- | --- |
| Wood Dust Fibers | 23% |
| Powdered limestone | 69% |
| Dextrin | 8% |
| Total | 100% |

EXAMPLE #2

| Components | Weight-% |
| --- | --- |
| Sawdust (Wood) | 30% |
| Titanium Dioxide | 58% |
| Tapioca Pearl Starch | 12% |
| Total | 100% |

EXAMPLES #3 AND #4

These are comparative Examples demonstrating dissolutions times and attrition results obtained with various granules, including a granule of the present invention.

| | Eco-granule QD | Eco-granule HW | Biodac |
| --- | --- | --- | --- |
| Wood fibers (weight-%) | 25% wood fibers | 25% wood fibers | Paper fibers and minerals. (Biodac is a granule made from paper sludge.) |
| Mineral filler (weight-%) | 68% CaCO$_3$ | 69% CaCO$_3$ | |
| Binder (weight-%) | 7% dextrin (from corn) | 6% modified pre-gel starch | |
| Dissolve time | 15 seconds | 4 hours | Did not dissolve |
| Attrition results | 97% | 98.6% | 99% |

The dissolving test was carried out as follows: Five grams of granules were added to 40 cc of water in a cup, at which time a stopwatch was actuated. The cup was swirled gently every 5 minutes, and the watch was stopped when the granules dissolved. The attrition tests were carried out in accordance with ASTM E728-97.

EXAMPLE #5

Use as a Carrier 100 pounds of granules of Example 1 along with 5 pounds of carbaryl (Sevin) pesticide in powder form are dosed in turn from a weighing station into a hopper. The unmixed batch is conveyed to a plowshare high-speed mixer, where it is mixed for from 90 to 120 seconds in a plowshare high-speed mixer to provide a product that can be used to deliver the carbaryl pesticide to lawns and that will dissolve or disintegrate after it is subjected to ¼ inch of rain or equivalent moisture.

What is claimed is:
1. A quickly dissolving carrier granule consisting of
12-40 weight-% of wood fibers having a bulk density of less than 20 pounds per cubic foot, wherein the wood fibers range from about 10 microns to about 2 mm in length and wherein at least 35 weight-% of said fibers are retained on a 50-Mesh U.S. Sieve Series screen,
50-85 weight-% of mineral filler having a bulk density of 65-75 pounds per cubic foot, the amount of said mineral filler being selected so that the weight ratio of wood fiber to mineral filler in the granule ranges from 18:82 through 25:75, and 3-12 weight-% of a dextrin binder, wherein said granule has a bulk density in the range 38-42 pounds per cubic foot, said granule passes through a 10-Mesh U.S. Sieve Series screen and is retained on a 40-Mesh U.S. Sieve Series screen, said granule has a moisture content of less than 5 weight-%, said granule has a Resistance to Attrition of at least 90%, and said granule is completely dissolved in less than 5 minutes when immersed in water.

2. The quickly dissolving carrier granule of claim 1, wherein said wood fibers are derived from a source that does not contain urea-formaldehyde resin or diphenylmethane diisocyanate resin.

3. The quickly dissolving carrier granule of claim 1, wherein the mineral filler is selected from the group consisting of kaolin, titanium dioxide, sodium bicarbonate, calcium carbonate, lime, fly ash, dolomite, gypsum, and mixtures thereof.

4. The quickly dissolving carrier granule of claim 1, wherein the mineral filler is calcium carbonate or lime having a particle size in the range 10 to 100 microns.

5. A carrier granule composition comprising from 10 to 90 weight-% of a carrier granule comprising 12-40 weight-% of wood fibers having a bulk density of less than 20 pounds per cubic foot, 50-85 weight-% of mineral filler having a bulk density of 65-75 pounds per cubic foot, and 3-12 weight-% of a dextrin binder, wherein said granule has a bulk density in the range 38-42 pounds per cubic foot, said granule passes through a 10-Mesh U.S. Sieve Series screen and is retained on a 40-Mesh U.S. Sieve Series screen, said granule has a moisture content of less than 5 weight-%, said granule has a Resistance to Attrition of at least 90%, and said granule is completely dissolved in less than 5 minutes when immersed in water, and from 90 to 10 weight-% of a carrier granule comprising 12-40 weight-% of wood fibers having a bulk density of less than 20 pounds per cubic foot, 50-85 weight-% of mineral filler having a bulk density of 65-75 pounds per cubic foot, and 3-12 weight-% of a food-based or industrial-based native starch binder, wherein said granule has a bulk density in the range 38-42 pounds per cubic foot, said granule passes through a 10-Mesh U.S. Sieve Series screen and is retained on a 40-Mesh U.S. Sieve Series screen, said granule has a moisture content of less than 5 weight-%, said granule has a Resistance to Attrition of at least 90%, and said granule is completely dissolved in less than 5 minutes when immersed in water.

6. A quickly dissolving carrier granule consisting of 15.84 to 24.25 weight-% of wood fibers having a bulk density of less than 20 pounds per cubic foot, wherein the wood fibers range from about 10 microns to about 2 mm in length and wherein at least 35 weight-% of said fibers are retained on a 50-Mesh U.S. Sieve Series screen, 66 to 79.54 weight-% of granite fines having a bulk density of 65-75 pounds per cubic foot, the amount of the granite fines being selected so that the weight ratio of wood fiber to granite fines in the granule ranges from 18:82 through 25:75, and 3-12 weight-% of a dextrin binder, wherein said granule has a bulk density in the range 38-42 pounds per cubic foot, said granule passes through a 10-Mesh U.S. Sieve Series screen and is retained on a 40-Mesh U.S. Sieve Series screen, said granule has a moisture content of less than 5 weight-%, said granule has a Resistance to Attrition of at least 90%, and said granule is completely dissolved in less than 5 minutes when immersed in water.

7. The quickly dissolving carrier granule of claim 6, wherein the granite fines has a particle size in the range 10 to 100 microns.

8. The quickly dissolving carrier granule of claim 6, wherein said wood fibers are derived from a source that does not contain urea-formaldehyde resin or diphenylmethane diisocyanate resin.

9. A carrier granule composition comprising from 10 to 90 weight-% of a carrier granule consisting of 15.84 to 24.25 weight-% of wood fibers having a bulk density of less than 20 pounds per cubic foot, 66 to 79.54 weight-% of granite fines having a bulk density of 65-75 pounds per cubic foot, and 3-12 weight-% of a dextrin binder, wherein said granule has a bulk density in the range 38-42 pounds per cubic foot, said granule passes through a 10-Mesh U.S. Sieve Series screen and is retained on a 40-Mesh U.S. Sieve Series screen, said granule has a moisture content of less than 5 weight-%, said granule has a Resistance to Attrition of at least 90%, and said granule is completely dissolved in less than 5 minutes when immersed in water, and from 90 to 10 weight-% of a carrier granule consisting of 12-40 weight-% of wood fibers having a bulk density of less than 20 pounds per cubic foot, 50-85 weight-% of mineral filler having a bulk density of 65-75 pounds per cubic foot, and 3-12 weight-% of a food-based or industrial-based native starch binder, or from 90 to 10 weight-% of a carrier granule consisting of 15.84 to 24.25 weight-% of wood fibers having a bulk density of less than 20 pounds per cubic foot, 66 to 79.54 weight-% of granite fines having a bulk density of 65-75 pounds per cubic foot, and 3-12 weight-% of a food-based or industrial-based native starch binder, wherein said granule has a bulk density in the range 38-42 pounds per cubic foot, said granule passes through a 10-Mesh U.S. Sieve Series screen and is retained on a 40-Mesh U.S. Sieve Series screen, said granule has a moisture content of less than 5 weight-%, said granule has a Resistance to Attrition of at least 90%, and said granule is completely dissolved in less than 5 minutes when immersed in water.

\* \* \* \* \*